United States Patent
Damaser et al.

(10) Patent No.: US 11,207,013 B2
(45) Date of Patent: Dec. 28, 2021

(54) SYSTEMS AND METHODS FOR ESTIMATING A VOLUME OF A HOLLOW ORGAN

(71) Applicants: THE CLEVELAND CLINIC FOUNDATION, Cleveland, OH (US); THE U.S. GOVERNMENT AS REPRESENTED BY THE DEPT. OF VETERN AFFAIRS, Washington, DC (US)

(72) Inventors: Margot S. Damaser, Cleveland Heights, OH (US); Steve Majerus, Cleveland, OH (US)

(73) Assignees: THE CLEVELAND CLINIC FOUNDATION, Cleveland, OH (US); THE DEPARTMENT OF VETERANS AFFAIRS, Washington, DC (US)

( * ) Notice: Subject to any disclaimer, the term of this patent is extended or adjusted under 35 U.S.C. 154(b) by 690 days.

(21) Appl. No.: 16/074,149

(22) PCT Filed: Jan. 26, 2017

(86) PCT No.: PCT/US2017/015049
§ 371 (c)(1),
(2) Date: Jul. 31, 2018

(87) PCT Pub. No.: WO2017/136212
PCT Pub. Date: Aug. 10, 2017

(65) Prior Publication Data
US 2021/0121111 A1   Apr. 29, 2021

Related U.S. Application Data
(60) Provisional application No. 62/289,622, filed on Feb. 1, 2016.

(51) Int. Cl.
   *A61B 5/20* (2006.01)
   *A61B 5/00* (2006.01)
   (Continued)

(52) U.S. Cl.
   CPC ............ *A61B 5/204* (2013.01); *A61B 5/0084* (2013.01); *A61B 5/053* (2013.01); *A61B 5/1076* (2013.01);
   (Continued)

(58) Field of Classification Search
   CPC .. A61B 5/03; A61B 5/20; A61B 5/202; A61B 5/204; A61B 5/205; A61B 5/208;
   (Continued)

(56) References Cited

U.S. PATENT DOCUMENTS 4,926,871 A * 5/1990 Ganguly ................. A61B 5/204
                                                       600/443
8,097,851 B2 * 1/2012 Chang ....................... G01J 1/44
                                                       250/338.4
(Continued)

FOREIGN PATENT DOCUMENTS

JP          4643089 B2 *  3/2011 ......... A61B 1/00156
WO    WO-2014160517 A1 * 10/2014 ........... A61B 5/6874

OTHER PUBLICATIONS

B. C. Gill, P. C. Fletter, P. J. Zaszczurynski, A. Perlin, D. Yachia and M. S. Damaser, "Fluid Volume Conductance for Determination of Bladder Volume," 2006 3rd IEEE/EMBS International Summer School on Medical Devices and Biosensors, Cambridge, MA, USA , 2006, pp. 115-117 (Year: 2006).*

*Primary Examiner* — Patrick Fernandes
*Assistant Examiner* — Severo Antonio P Lopez
(74) *Attorney, Agent, or Firm* — Tarolli, Sundheim, Covell & Tummino LLP

(57) ABSTRACT

The present disclosure relates generally to estimating an interior diameter of a hollow organ. As such, one aspect of
(Continued)

the present disclosure relates to a system that can include a light-based distance sensor and a device housing the light-based distance sensor located within the hollow organ. The light-based distance sensor can include an emitter and a detector. The emitter can transmit a conical beam of light to an inner surface of a hollow organ. The detector can receive a portion of the light back-reflected from the inner surface of the hollow organ. The device can determine a volume of the hollow organ based on a signal related to the back-reflected portion of the light, which can be based on a distance between the light-based distance sensor and the inner surface of the hollow organ.

7 Claims, 5 Drawing Sheets

(51) Int. Cl.
*A61B 5/053* (2021.01)
*A61B 5/107* (2006.01)

(52) U.S. Cl.
CPC .... *A61B 5/1079* (2013.01); *A61B 2562/0247* (2013.01)

(58) Field of Classification Search
CPC ..... A61B 5/0084; A61B 5/053; A61B 5/0538; A61B 5/107; A61B 5/1073; A61B 5/1076; A61B 5/1079; A61B 2562/0247; A61B 5/6871; A61B 5/6874
See application file for complete search history.

(56) References Cited

U.S. PATENT DOCUMENTS

| | | | |
|---|---|---|---|
| 8,439,822 B2* | 5/2013 | Shigemori | A61B 1/041 600/103 |
| 8,858,460 B2* | 10/2014 | Connors | A61B 5/72 600/561 |
| 2010/0121161 A1* | 5/2010 | Robertson | A61B 5/205 600/302 |
| 2015/0285625 A1* | 10/2015 | Deane | G01S 7/4863 348/140 |

* cited by examiner

SYSTEMS AND METHODS FOR ESTIMATING A VOLUME OF A HOLLOW ORGAN

RELATED APPLICATIONS

This application claims the benefit of U.S. Provisional Application No. 62/289,622, entitled "SYSTEMS AND METHODS FOR ESTIMATING A VOLUME OF A HOLLOW ORGAN," filed Feb. 1, 2016. The entirety of this application is hereby incorporated by reference for all purposes.

TECHNICAL FIELD

The present disclosure relates generally to estimating a volume of a hollow organ and, more specifically, to systems and methods that employ light (e.g., infrared light, laser light, visible incoherent light, or the like) sensing to measure a distance to an interior wall of a hollow organ, which is used to estimate the volume of the hollow organ.

BACKGROUND

One example of a hollow organ is the urinary bladder (or "bladder"), which stores urine. The bladder fills with urine until nerves associated with the bladder cause an urge to urinate. In a healthy bladder, upon urination, the bladder empties completely without any leakage. However, different urological conditions, including: overactive bladder, urinary incontinence, neurogenic bladder, underactive bladder, benign prostatic hyperplasia, and the like, can cause bladder dysfunction, including leakage, incomplete emptying, incontinence, and the like.

Many urological conditions can be diagnosed based on one or more conventional urodynamic tests, such as cystometrography. However, these conventional urodynamic tests merely provide a snapshot of urodynamic functions in an artificial, non-physiological, uncomfortable environment. In many cases, symptoms discovered with such conventional urodynamic tests cannot be reproduced. As an alternative to conventional urodynamic tests, ambulatory urodynamic tests can be conducted under normal physiologic conditions. However, these ambulatory urodynamic tests are expensive and their results suffer from questionable accuracy.

SUMMARY

The present disclosure relates generally to estimating a volume of a hollow organ and, more specifically, to systems and methods that employ light (e.g., infrared light, laser light, visible incoherent light, or the like) sensing to measure a distance to an interior wall of a hollow organ, which is used to estimate the volume of the hollow organ.

In one aspect, the present disclosure includes a system that can estimate a volume of a hollow organ. The system can include a distance sensor that detects light and a device housing the distance sensor located within the hollow organ. The distance sensor can include an emitter, which can transmit a conical beam of light to an inner surface of a hollow organ, and a detector, which can receive a portion of the light back-reflected from the inner surface of the hollow organ. The device can estimate the volume of the hollow organ based on a signal related to the back-reflected portion of the light, which can be based on a distance between the distance sensor and the inner surface of the hollow organ.

In another aspect, the present disclosure includes a method for estimating the volume of the hollow organ. The method can include transmitting a conical beam of light from an emitter of a sensor to an inner surface of the hollow organ. The method can also include receiving a portion of the light back-reflected from the inner surface of the hollow organ at a receiver of the sensor, wherein the sensor is located within the hollow organ. The method can further include determining a distance between the sensor and the inner surface of the hollow organ based on the portion of the light back-reflected to the receiver; and determining the volume of the hollow organ based on the distance between the sensor and the inner surface of the hollow organ.

One example of the hollow organ is the urinary bladder, and the systems and methods of the present invention can use light sensing to measure the interior diameter of the bladder, which can be used, for example, in the determination of a volume of the bladder. According to another aspect, the present disclosure includes a method for tracking bladder pressure and bladder volume to facilitate diagnosis of a bladder dysfunction. The method can include determining bladder pressure at a plurality of points over a time period and determining corresponding bladder volumes at the plurality of points over the time period based on information sensed by a distance sensor located within the bladder. The method can also include determining a subset of bladder pressures and corresponding bladder volumes corresponding to a time segment during the time period; and sending the subset of bladder pressures and corresponding bladder volumes to an external device.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
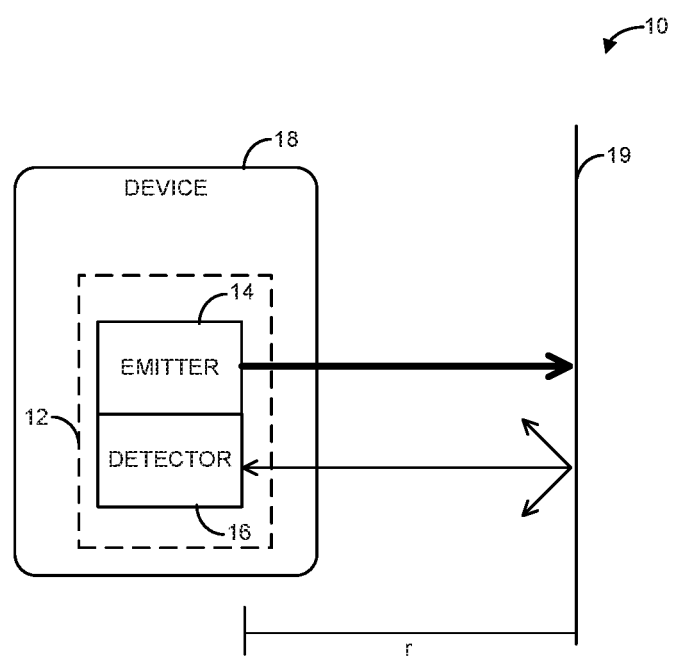
FIGS. 1-2 are schematic block diagrams, each showing an example of a system that can estimate a volume of a hollow organ in accordance with an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "hollow organ" can refer to a hollow tube, pouch, or cavity which serves a bodily function. Examples of hollow organs can include the bladder, the heart, the stomach, the intestines, and the like.

As used herein, the term "bladder" can refer to the "urinary bladder", a hollow organ that collects urine before disposal by urination. The bladder can exhibit a bladder volume and a bladder pressure, which can be measured.

As used herein, the term "lumen" can refer to the interior of a hollow organ.

As used herein, the term "light" can refer electromagnetic radiation, including infrared light, near-infrared light, laser light, visible incoherent light, or the like.

As used herein, the term "infrared" can refer to electromagnetic radiation with a longer wavelength than visible light. It will be understood that the term "infrared" can also include "near infrared" electromagnetic radiation.

As used herein, the term "infrared sensor" can refer to an electronic device that emits and detects infrared radiation to determine a distance to a wall of a hollow organ.

As used herein, the term "back-reflected" can refer to the amount of electromagnetic radiation (e.g., infrared light) reflected back on axis to a sensor from a particular point. The amount of electromagnetic radiation back-reflected to the sensor can correlate to the distance traveled by the electromagnetic radiation.

As used herein, the term "dysfunction" can refer to an abnormality or impairment of a specified bodily organ (e.g., the bladder).

As used herein, the term "urodynamics" can refer to a study assessing how the bladder and urethra are performing their job of storing and releasing urine.

As used herein, the term "ambulatory urodynamics" can refer to any functional test of the lower urinary tract predominantly utilizing natural filling of the urinary tract. Ambulatory urodynamics is different from conventional urodynamics, which uses artificial, non-physiological filling of the bladder.

As used herein, the term "artifact" can refer to a feature of a signal that is not naturally present. One example of a type of artifact is a motion artifact.

As used herein, the term "motion artifact" can refer to an error in a signal due to motion. For example, the motion artifact can be due to the patient coughing, laughing, bending, or the like.

As used herein, the term "subject" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein.

II. Overview

The present disclosure relates generally to estimating a volume of a hollow organ. More specifically, the present disclosure relates to systems and methods that employ light-based distance sensing (where the light may be infrared light, near-infrared light, laser light, visible incoherent light, or the like) to measure a distance to an interior wall of the hollow organ, which can be used to estimate the volume of the hollow organ. For example, assuming that the hollow organ is spherically shaped, so that the volume can be calculated as $4\pi(r^3/3)$, where r is the distance between the light-based distance sensor and an interior wall of the hollow organ.

A patient's bladder is one example of the hollow organ. For example, the volume of the bladder can be determined by a device (either buoyant or non-buoyant). In the buoyant example, the device can include a central rigid section containing active electronics and an exterior flexible balloon filled with a buoyant liquid or gas, floating within the bladder lumen. A light-based distance sensor can be mounted on and/or within the central rigid section, which can determine the volume of the urinary bladder based on the estimate of the distance between the light-based distance sensor and the interior wall of the bladder. In the non-buoyant example, a flexible portion of a different shape and functionality can take the place of the flexible balloon, and the device can sink to a known location at the bottom of the bladder. In either case, the device can be used to facilitate ambulatory urodynamics.

III. Systems

One aspect of the present disclosure can include a system 10 (FIG. 1) that can determine one or more values that can be used to estimate a volume of a hollow organ. It will be understood that FIG. 1 is drawn schematically for ease of illustration and explanation and not drawn to scale or with regard to specificity of shape. One example of the hollow organ can include the urinary bladder. In this example, by estimating the volume of the urinary bladder (assuming a spherical shape, so that the volume can be calculated as $4\pi(r^3/3)$, where r is the distance from detector 16 to an interior wall of the bladder), the system 10 can provide increased context for the use of ambulatory urodynamics. In fact, the system 10 can increase the accuracy of ambulatory urodynamics.

In addition to the urinary bladder, the hollow organ can be any other hollow organ located within a patient's body. Accordingly, the system 10 can be substantially biocompatible. In other words, at least a portion of the system 10 can be made of a biocompatible material, coated with a biocompatible material, and/or housed within a biocompatible material. Additionally, at least a portion of the system 10 can be enclosed in a water proof or water resistant housing. For example, when the hollow organ is the urinary bladder, the system 10 can float in urine within the bladder lumen, requiring at least a portion of the system 10 to be water proof or water resistant to prevent damage to portions of the system 10.

The system 10 can include a light-based distance sensor 12 and a device 18 housing the light-based distance sensor 12. For example, device 18 can house the light-based distance sensor 12 on or within the device 18. In either case, the light-based distance sensor 12 can be protected from damage from fluid within the hollow organ. The device 18 can be sized to permit insertion into the hollow organ (e.g., when the hollow organ is the urinary bladder, a conventional 24-26 French cystoscope can be used to insert the device 18 into the urinary bladder).

The device 18 can include a portion that includes active electronics (the portion can be "rigid" in that the portion is more rigid than other portions of the device). For example, this portion can be a flexible circuit board or a more rigid circuit board. The light-based distance sensor 12 can be embodied on or within this portion. For example, this portion can include an integrated circuit chip, such as an application-specific integrated circuit (ASIC) chip, an integrated system-on-chip (SoC), or the like. The integrated circuit chip can embody at least the active electronics and/or the light-based distance sensor 12. In addition to the active electronics, the integrated circuit chip can also include one or more of a wireless transmitter, a wireless receiver, a wireless transceiver, a micro battery, a battery recharging component, a power control component, an analog-to-digital convertor, one or more controllers, etc. The device 18 can include an orienting weight at least to ensure that the light-based distance sensor 12 is always oriented in a specific manner. In some instances, the micro battery can be used as the orienting weight for the device 18.

The device 18 can also include a non-rigid portion that includes a deformable flexible member (e.g., a balloon or other flexible form). The deformable flexible member can help to ensure that the device 18 is not easily expelled from the hollow organ. For example, the non-rigid portion can be deformed to fit inside a device for insertion into the hollow organ and reform to expand within the hollow organ. However, the deformable flexible member can be buoyant or non-buoyant. For example, the non-rigid portion can be at least partially filled with a buoyant liquid (e.g., mineral oil) or gas (e.g., carbon dioxide) that allows the device 18 to float in a fluid within the hollow organ and not be expelled from the hollow organ. As another example, the non-rigid portion can be non-buoyant so that the device 18 sinks to the bottom of the hollow organ. The portion of the device 18, in some instances, can be centrally located, while the non-rigid section can be located at the exterior of the device 18. In other instances, the portion of the device 18 can be oriented at the top of the device 18, while the non-rigid section can be oriented at the bottom of the device 18. In any instance, the rigid portion and the non-rigid portion can be at least partially coupled together into the device 18.

In cases where the hollow organ is the urinary bladder, the non-rigid portion of the device 18 can be buoyant, so to enable the device 18 to float in urine located within the urinary bladder, yet not be expelled upon voiding. However, the non-rigid portion can also be non-buoyant so that the device 18 sinks to the bottom of the bladder, yet is not expelled upon voiding. The active electronics of the rigid portion can determine properties of the bladder (e.g., the diameter of the bladder, bladder volume, bladder pressure, and the like). For example, the bladder pressure can be determined by measuring the internal pressure of the non-rigid portion (e.g., the balloon). The bladder volume can be estimated based on a measurement the distance from the light-based distance sensor 12 on the device 18 to the opposite wall of the bladder. The internal weight (e.g., the battery) can automatically re-orient the device 18 to reduce rotation and reduce noise during measurements corresponding to the distance in ambulatory subjects.

The light-based distance sensor 12 can emit and detect one or more of infrared light, near-infrared light, laser light, visible incoherent light, or the like. The light-based distance sensor 12 can include an emitter 14 and a detector 16. It will be understood that FIG. 1 is drawn schematically for ease of illustration and explanation and not drawn to scale. In some instances, the emitter 14 can be a light emitting diode, while the detector 16 can be a photodiode or a phototransistor. The emitter 14 can transmit a conical beam of light to a point on an inner surface of an opposing side wall of the hollow organ. The detector 16 can receive a portion of the light back-reflected from the point on the inner surface 19 of the hollow organ. Other portions of the light radiation can be scattered along other lines. The detected back-reflected portion of the light can correlate to the distance (r) between the detector 16 and the wall (inner surface 19) of the hollow organ.

The detector 16 can send a signal that includes information related to the detected back-scattered light to the active electronics of the device 18, which can determine a diameter of the hollow organ based on the signal related to the back-reflected portion of the light. For example, based on the back-reflected portion of the light (and, in some instances, knowledge of an amount of the light emitted), the radius (r) corresponding to the distance between the detector 16 and the wall (inner surface 19) of the hollow organ can be determined. The hollow organ can be approximated as a sphere, so that the volume of the hollow organ can be estimated based on the radius (r) of the hollow organ (or $V=4\pi(r^3/3)$).

In some instances, the estimate of the volume can be further based on a conductance within the bladder. The conductance can be measured between two electrodes placed inside the bladder. In some instances, the electrodes can be part of or affixed to the device 18. However, in other instances, the electrodes need not be part of or affixed to the device. By combining the conductance values and the distance (r) value, superior sensitivity over a wide range of bladder diameters and urine properties can be obtained.

Figure 2:
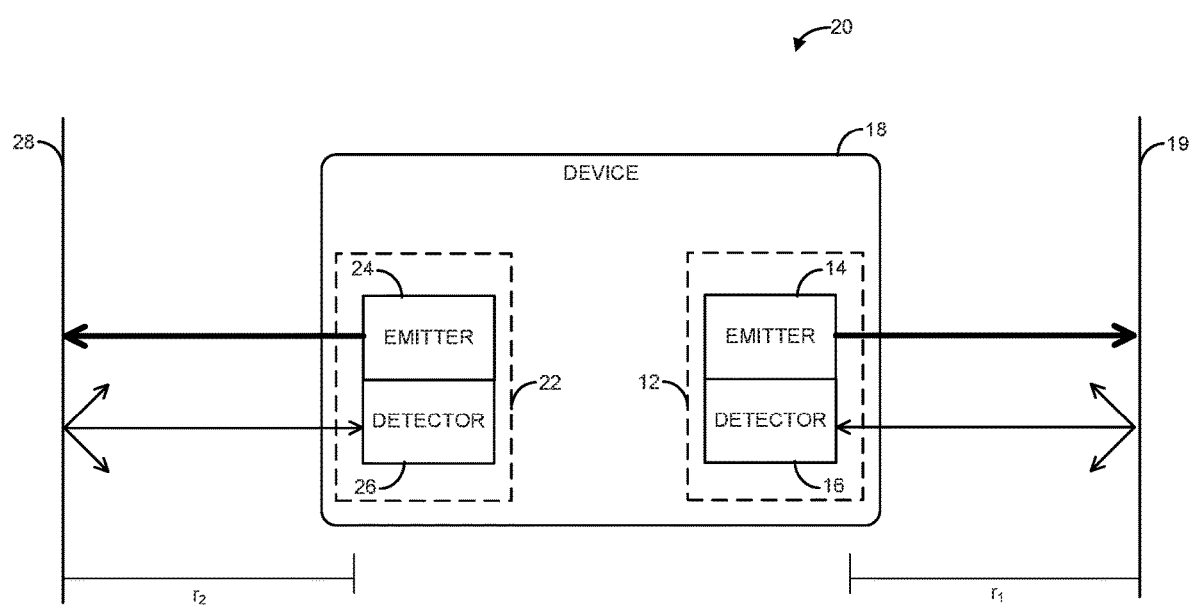

Another system 20 for estimating the diameter of the hollow organ is shown in FIG. 2. It will be understood that FIG. 2 is drawn schematically for ease of illustration and explanation and not drawn to scale. The system 20 can include two light-based distance sensors 12, 22 located on different polar ends of the device 18 (either in the horizontal direction, as illustrated, or in the vertical direction), each including an emitter 14, 24 and a detector 16, 26. The emitter 14, 24 of each of the two light-based distance sensors 12, 22 can transmit a conical beam of light to a respective portion of the inner surface 19, 28 of the hollow organ and receive respective back-reflected portions of light at the detector 16, 26 of each of the two light-based distance sensors 12, 22.

The device 18 can determine distances ($r_1$, $r_2$) between respective portions of the light-based distance sensors 12, 22 (e.g., detectors 16, 26) and the respective portions of the inner surface 19, 28 of the hollow organ. The device 18 can determine a diameter of the bladder by summing the distances ($r_1+r_2$) and the estimation of the volume is more accurate, especially in ambulatory settings, because of this differential measurement. Accordingly, the volume of the bladder can be approximated using the spherical approximation as: $V=4\pi((r_1+r_2)/2)^3/3)$.

When the hollow organ is the urinary bladder, the volume estimation of systems 10 and 20 provides several advantages with regard to ambulatory urodynamics and stimulation. Indeed, understanding the full bladder function (pressure and volume) context can improve understanding of the neurophysiology of bladder control and bladder dysfunctions. The systems 10, 20 enhance the accuracy of a computer-diagnosis algorithm for various bladder dysfunctions, which can be used for ambulatory urodynamics. The volume estimated by the systems 10, 20 can also be used to control various bladder functions according to a specialized computer algorithm. Moreover, the estimated volume by the systems 10, 20 can enhance the context for bladder pressure data (determined by a pressure sensor either within or separate from the device 18), allowing a computer algorithm the ability to better determine the state of the bladder (e.g., voiding contractions, non-voiding, or non-voiding urgency contractions).

IV. Methods

Another aspect of the present disclosure can include methods 30, 40 (FIGS. 3 and 4) for estimating an interior diameter of a hollow organ. In some instances, the hollow organ can be the urinary bladder. One example of a method 50 for tracking bladder pressure and bladder volume to facilitate diagnosis of bladder dysfunction (e.g., through ambulatory urodynamics) is shown in FIG. 5.

The methods 30-50 are illustrated as process flow diagrams with flowchart illustrations, which can be implemented by one or more components of the systems 10 and 20, as shown in FIGS. 1 and 2. For purposes of simplicity, the methods 30-50 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30-50.

Figure 3:
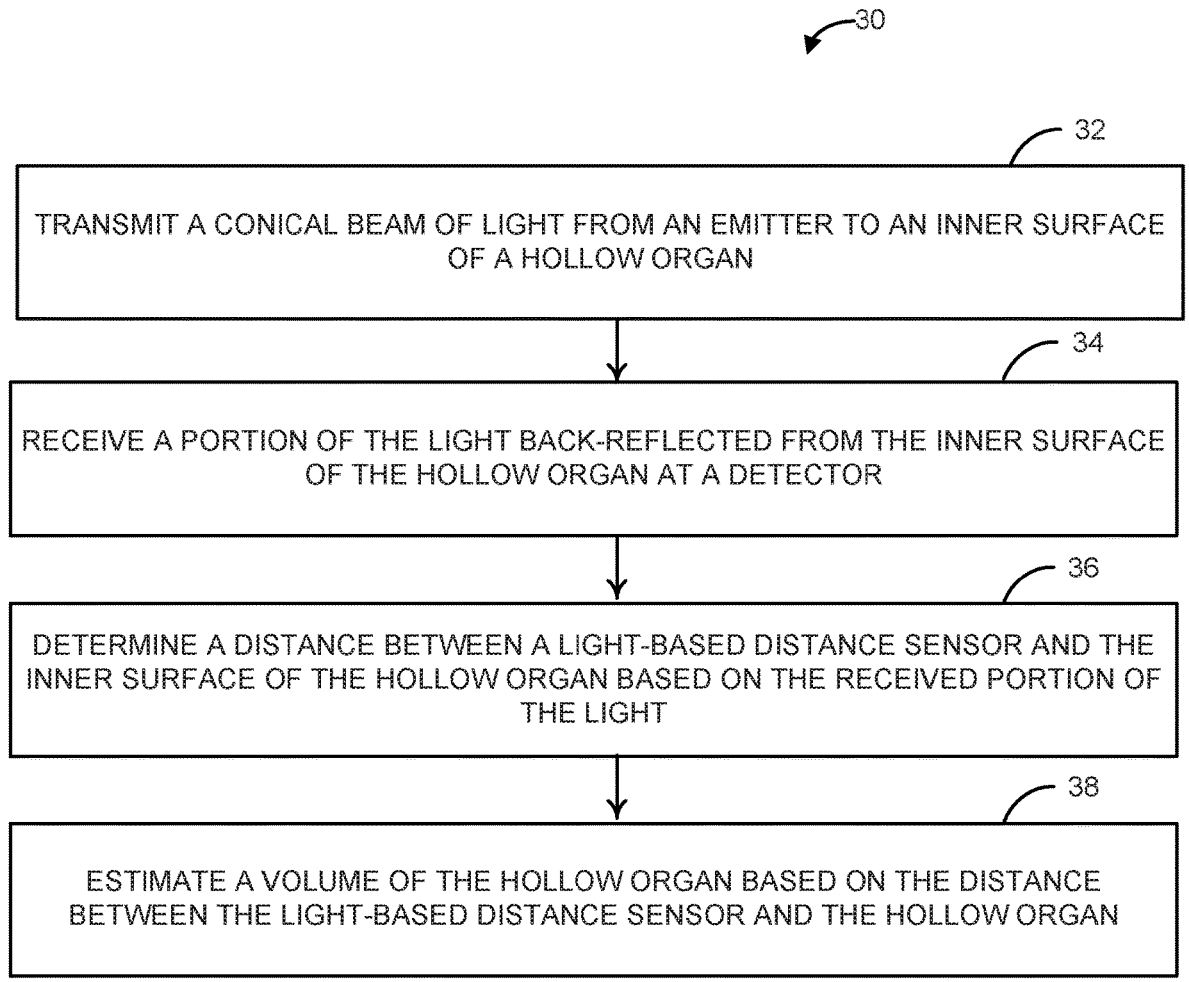
FIGS. 3-4 are process flow diagrams, each illustrating example methods for estimating a volume of a hollow organ in accordance with another aspect of the present disclosure.

Referring now to FIG. 3, illustrated is a method 30 for estimating a volume of a hollow organ. The volume can be estimated by a device 18 that houses one or more light-based distance sensors (emitting and detecting, for example, infrared light, laser light, visible incoherent light, or the like). All components of the device 18 can be located within the hollow organ. For example, the hollow organ can be the urinary bladder, and the device 18 can float within urine housed inside the urinary bladder. In other instances, the device 18 can be non-buoyant so that the device 18 sinks in the urinary bladder.

At 32, a conical beam of light can be transmitted from an emitter of a light-based distance sensor to an inner surface of a hollow organ. At 34, a portion of the light back-reflected from the inner surface of the hollow organ can be received at a receiver of the sensor. The back-reflected portion of the light is reflected from a portion of the inner surface of the hollow organ that is on-axis with the light-based distance sensor, while the rest of the light is scattered away at other angles. At 36, a distance between the light-based distance sensor and the inner surface of the hollow organ can be determined based on the portion of the light back-reflected to the receiver. At 38, a volume of the hollow organ can be estimated based on the distance between the light-based distance sensor and the inner surface of the hollow organ. For example, the hollow organ can be approximated as a sphere, so that the volume can be estimated as $4\pi(r^3/3)$. In some instances, the volume can also be based on a conductance detected within the hollow organ (e.g., a conductance of urine inside the urinary bladder). The conductance of urine, for example, can be measured as a conductivity based on electrolyte concentration in the urine.

Figure 4:
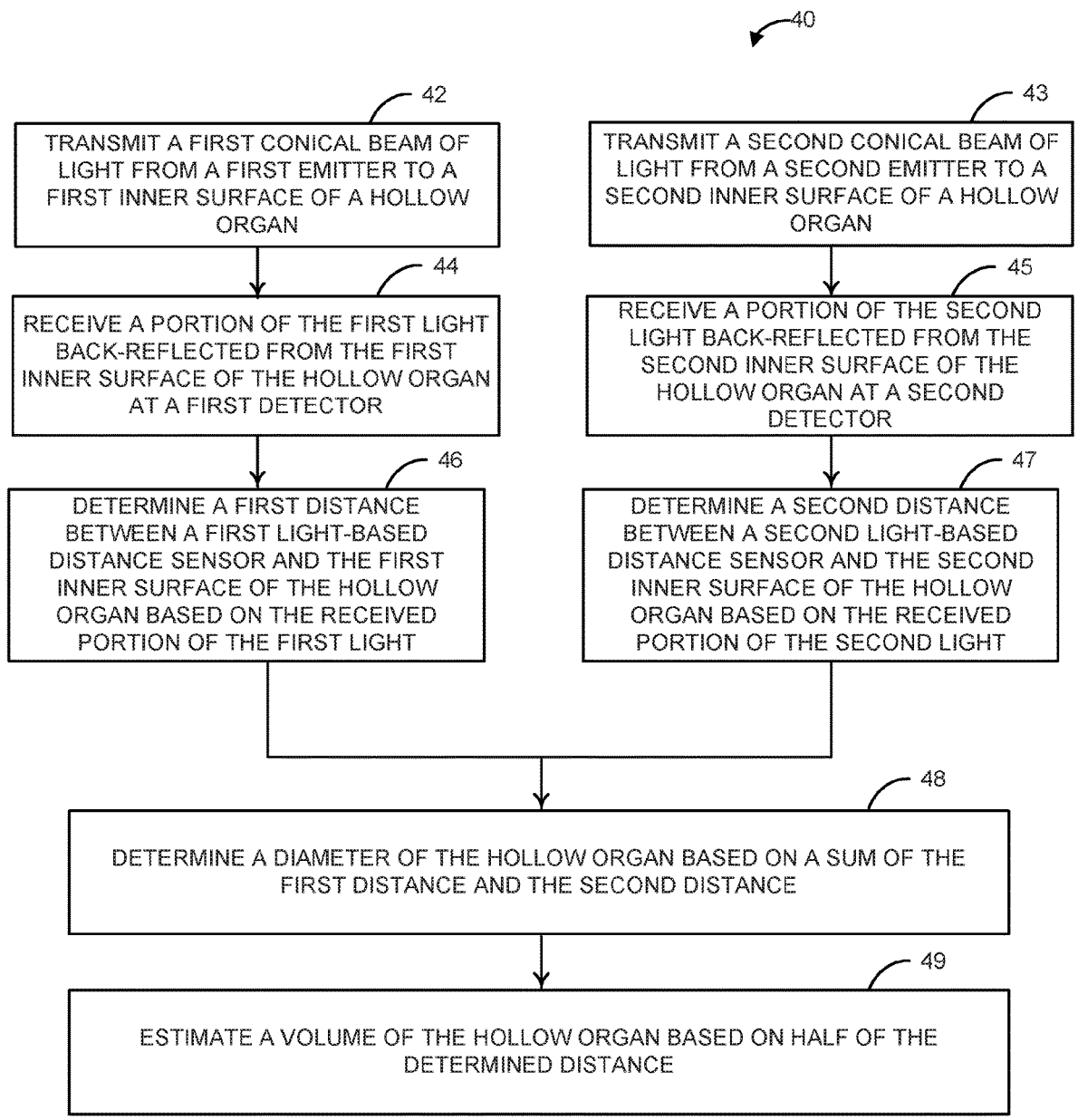
Figure 5:
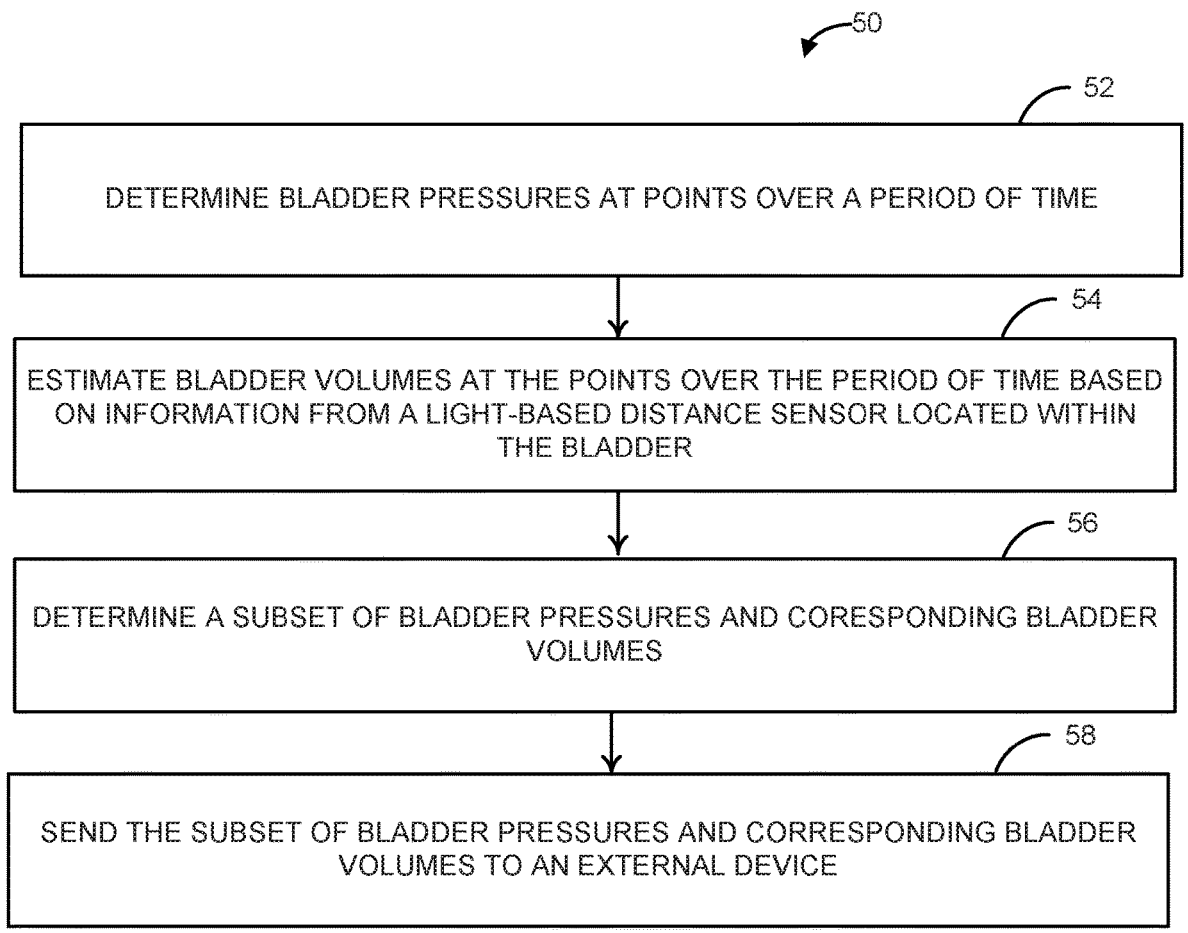
FIG. 5 is a process flow diagram illustrating a method for tracking bladder pressure and bladder volume to facilitate diagnosis of a bladder dysfunction in accordance with yet another aspect of the present disclosure.

FIG. 4 shows an alternate method 40 for estimating the volume of the hollow organ. In this case, the device 18 can include two different light-based distance sensors located at polar opposites of the device. The estimate of the volume in this case is more accurate and accounts for motion artifact.

At 42, a first conical beam of light can be transmitted from a first emitter to a first inner surface of the hollow organ. At 44, a portion of the first light that is back-reflected from the first inner surface of the hollow organ can be received at the first receiver. At 46, a first distance between a first sensor and the first inner surface of the hollow organ can be determined.

At 43, a second conical beam of light can be transmitted from a second emitter to a first inner surface of the hollow organ. At 45, a portion of the second light that is back-reflected from the second inner surface of the hollow organ can be received at the first receiver. At 47, a second distance between a second light-based distance sensor and the second inner surface of the hollow organ can be determined. In some instances, steps 43, 45, and 47 can occur at the same time as steps 42, 44, and 46. However, steps 43, 45, and 47 can occur at a different (e.g., sequentially later) time than steps 42, 44, and 46.

At 48, a diameter of the hollow organ can be determined based on a sum of the first distance and the second distance. At 49, a volume of the hollow organ can be estimated based on half of the determined distance. In other words, the hollow organ can be approximated as a sphere, so that the volume can be estimated as $4\pi(((r_1+r_2)/2)^3/3)$. In some instances, the volume can also be based on a conductance detected within the hollow organ (e.g., a conductance or conductivity of urine inside the urinary bladder).

In some instances, the hollow organ can be the urinary bladder. Referring now to FIG. 5, illustrated is a method 50 for tracking bladder pressure and bladder volume to facilitate diagnosis of bladder dysfunction (e.g., through ambulatory urodynamics). At 52, bladder pressures can be determined at points over a period of time. At 54, bladder volumes can be estimated either at the points over the period of time or less frequently. Information from a light-based distance sensor located within the bladder (e.g., on or within device 18) can be used to estimate the bladder volume. At 56, a subset of bladder pressures and corresponding bladder volumes can be determined. For example, the subset can correspond to a time segment during the time period where something interesting is happening, such as a voiding or urgency contraction. At 58 the subset of bladder pressures and corresponding bladder volumes can be sent to an external device. A bladder dysfunction can be diagnosed based on the subset of bladder pressures and the corresponding bladder volumes. The diagnosis can be facilitated based on a comparison between the bladder pressure and a quantified metric for the specific type of bladder dysfunction. For example, a change in bladder volume can correspond to urine leakage at certain bladder pressures.

From the above description, those skilled in the art will perceive improvements, changes and modifications. Such improvements, changes and modifications are within the skill of one in the art and are intended to be covered by the appended claims.

What is claimed is:

1. A system comprising:
   a device configured to float within urine housed within a patient's bladder, the device comprising:
   a first portion that is within a water-resistant housing, the first portion comprising:
   a first light-based distance sensor located on a first polar end of the device, the first light-based distance sensor comprising:
   a first emitter, comprising a first infrared light emitting diode (LED), to transmit a conical beam of first light to a first inner surface of the patient's urinary bladder; and
   a first detector, comprising a first photodiode or a first phototransistor, to receive a portion of the first light back-reflected from the first inner surface of the patient's urinary bladder,
   wherein the portion of the first light back-reflected is based on a first distance between the first light-based distance sensor and the first inner surface of the patient's urinary bladder;
   a second light-based distance sensor located on a second polar end of the device, wherein the second polar end of the device is opposite of the first polar end, the second light-based distance sensor comprising:
  a second emitter, comprising a second infrared light emitting diode (LED), to transmit a conical beam of second light to a second inner surface of the patient's urinary bladder; and
  a second detector, comprising a second photodiode or a second phototransistor, to receive a portion of the second light back-reflected from the second inner surface of the patient's urinary bladder,
  wherein the portion of the second light back-reflected is based on a second distance between the second light-based distance sensor and the second inner surface of the patient's urinary bladder;
  electronics configured to determine a radius of the urinary bladder based on an average of the first distance between the first light-based distance sensor and the first surface of the patient's urinary bladder and the second distance between the second light-based distance sensor and the second surface of the patient's urinary bladder; and
  a battery configured to provide power to the first light-based distance sensor and the second light-based distance sensor, and further configured to act as an orienting weight for the device within the patient's urinary bladder to reduce movement of the device within the patient's urinary bladder; and
  a second portion that is non-rigid and configured to control a location of the device within the patient's urinary bladder.

2. The system of claim 1, wherein the first portion is configured to estimate a volume of the patient's urinary bladder based on the radius of the patient's urinary bladder, wherein the patient's urinary bladder is approximated as a sphere.

3. The system of claim 2, wherein the estimate of the volume of the patient's urinary bladder is further based on a conductance sensed within the patient's urinary bladder.

4. The system of claim 2, wherein the device further comprises a pressure sensor to detect a pressure within the patient's urinary bladder, wherein the electronics determine a state of the bladder based on the pressure and the estimated volume.

5. A method comprising:
transmitting a conical beam of first light from an emitter of a first light-based distance sensor to a first inner surface of a patient's urinary bladder, wherein the first light-based distance sensor is located on a first polar end of a device floating within urine housed inside the patient's urinary bladder;
receiving a portion of the light back-reflected from the first inner surface of the patient's urinary bladder at a receiver of the first light-based distance sensor, wherein the back-reflected portion of the first light is reflected from a portion of the first inner surface of the patient's urinary bladder that is on-axis with the first light-based distance sensor and a second light-based distance sensor, and the rest of the back-reflected first light is scattered away at other angles;
determining a first distance between the first light-based distance sensor and the first inner surface of the patient's urinary bladder based on the portion of the light back-reflected to the receiver;
transmitting a conical beam of second light from a second emitter of the second light-based distance sensor to a second part of the inner surface of the patient's urinary bladder, wherein the second light-based distance sensor is located on a second polar end of the device floating within urine housed inside the patient's urinary bladder, wherein the second polar end is opposite the first polar end;
receiving a portion of the second light back-reflected from the second part of the inner surface of the patient's urinary bladder at a second receiver of the second light-based distance sensor, wherein the back-reflected portion of the second light is reflected from a portion of the second inner surface of the patient's urinary bladder that is on-axis with the second light-based distance sensor, and the rest of the back-reflected second light is scattered away at other angles;
determining a second distance between the second light-based distance sensor and the second part of the inner surface of the patient's urinary bladder based on the portion of the second light back-reflected to the second receiver; and
estimating a volume of the patient's urinary bladder using a spherical approximation based on an average of the first distance between the first light-based distance sensor and the first surface of the patient's urinary bladder and the second distance between the second light-based distance sensor and the second surface of the patient's urinary bladder.

6. The method of claim 5, further comprising:
receiving a conductance of the urine inside the patient's urinary bladder; and
wherein the volume is further based on the conductance of the urine.

7. A method comprising:
determining bladder pressure at a plurality of points over a time period using a pressure sensor mounted on a device floating within urine housed inside the patient's urinary bladder;
determining corresponding bladder volumes at the plurality of points over the time period based on information sensed by two light-based distance sensors located within the bladder on the device, wherein the two light-based distance sensors are located on opposing polar ends of the device,
wherein the information sensed by the two light-based distance sensors comprises a distance value for each of the plurality of points,
wherein the distance value is determined by:
  transmitting a conical beam of light from an emitter of each of the two light-based distance sensors to inner surfaces of the patient's urinary bladder;
  receiving a portion of the light back-reflected from the inner surfaces of the patient's urinary bladder at a receiver of the two light-based distance sensors, wherein the distance value is based on the portion of the light back-reflected to the receiver from the inner surfaces of the patient's urinary bladder;
determining a subset of bladder pressures and corresponding bladder volumes corresponding to a time segment during the time period;
sending the subset of bladder pressures and corresponding bladder volumes to an external device; and
diagnosing a bladder dysfunction based on a comparison of bladder volumes corresponding to the subset of bladder pressures and a quantified metric for the bladder dysfunction.

* * * * *